United States Patent [19]

Thordarson

[11] 4,052,903

[45] Oct. 11, 1977

[54] PRESSURE SENSOR

[75] Inventor: Petur Thordarson, Seattle, Wash.

[73] Assignee: Thor Instrument Company, Inc., Seattle, Wash.

[21] Appl. No.: 747,488

[22] Filed: Dec. 6, 1976

[51] Int. Cl.$^2$ .............................................. G01L 7/08
[52] U.S. Cl. ...................................... 73/406; 73/409
[58] Field of Search ........................ 73/409, 406, 38, 73

[56] References Cited

U.S. PATENT DOCUMENTS

| | | | |
|---|---|---|---|
| 3,388,598 | 6/1968 | Hall | 73/406 |
| 3,574,284 | 4/1971 | Thordarson | 73/406 |

*Primary Examiner*—Donald O. Woodiel
*Attorney, Agent, or Firm*—Graybeal, Barnard & Uhlir

[57] ABSTRACT

A cup-shaped elastomeric diaphragm is snugly fitted onto an end portion of a support member which includes internal gas delivery and return passageways. A plurality of ports extend both radially and axially from the gas delivery passageway towards the diaphragm. A like number of identical gas return ports extend from another region of the diaphragm inwardly to the gas return passageway. A gas tight seal is provided between the diaphragm and the support member above the ports. In use the outer surface of the diaphragm is subjected to a pressure to be measured, e.g. subsurface hydrostatic pressure. A gas is delivered into the delivery passageway and through the sensor at a constant flow rate. The gas pressure expands the diaphragm in the regions of the ports to complete gas flow paths from the gas delivery ports to the gas return ports. The magnitude of the pressure to be measured acting on the diaphragm determines the gas pressure that is necessary to drive the gas through the sensor at a constant flow rate. The driving pressure of the gas is measured and is used to determine the magnitude of the pressure that is being measured.

10 Claims, 8 Drawing Figures

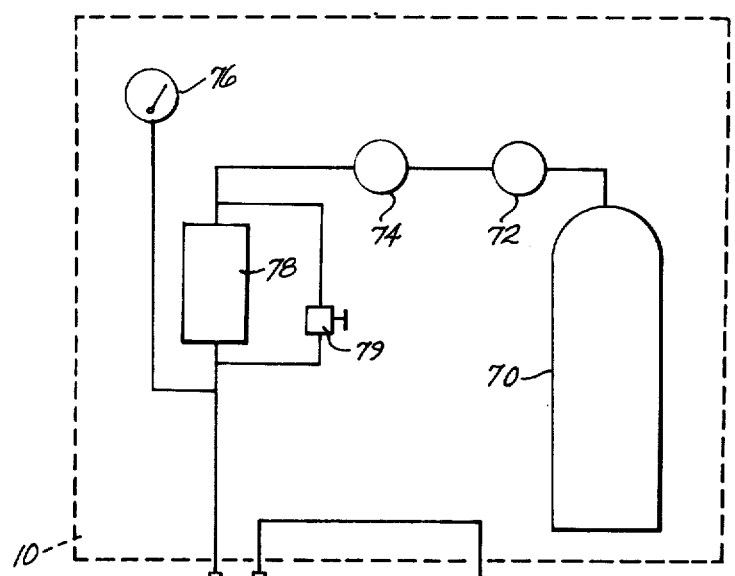
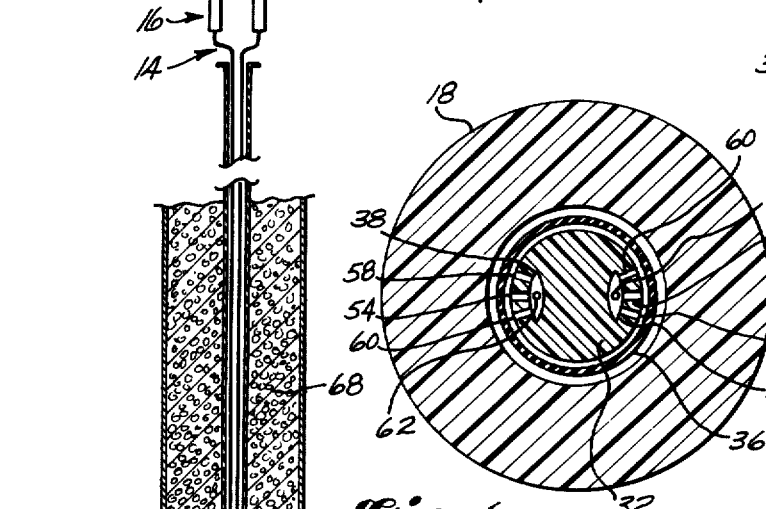
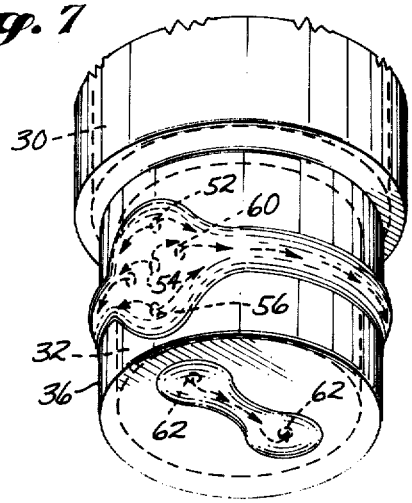
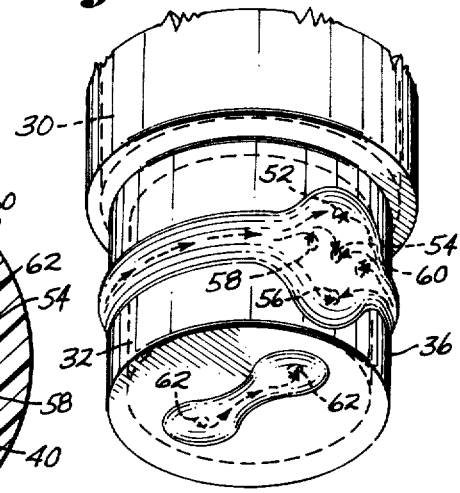
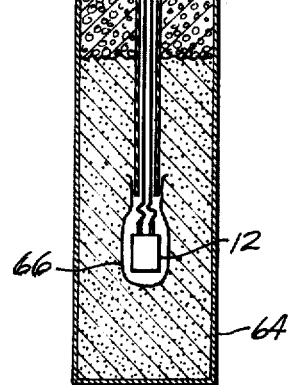
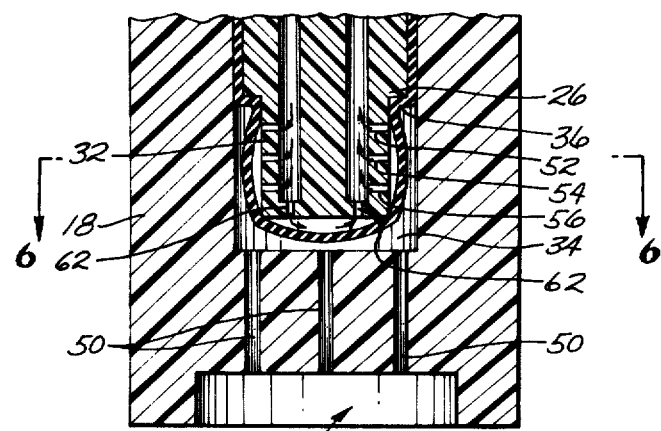

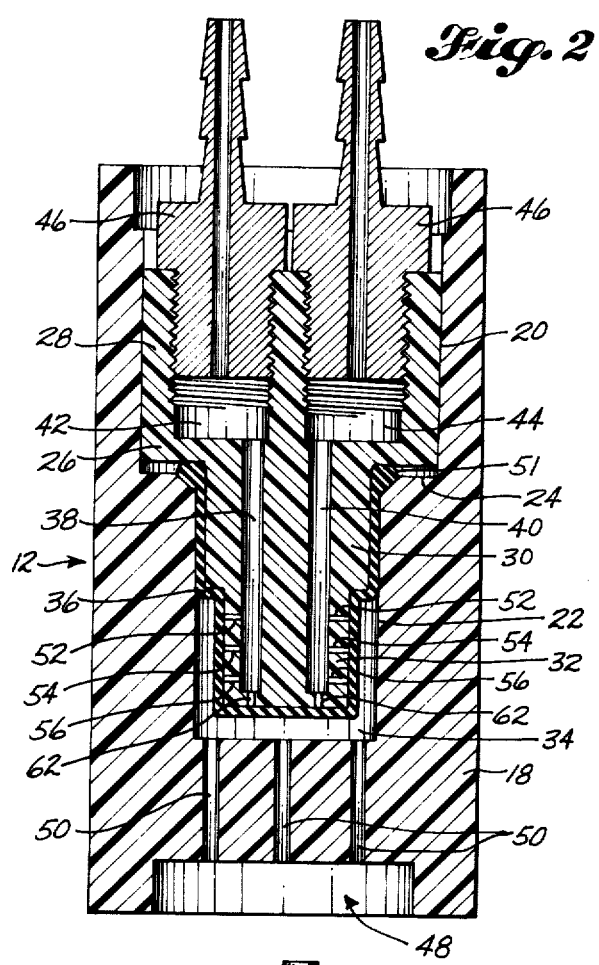
Fig. 2
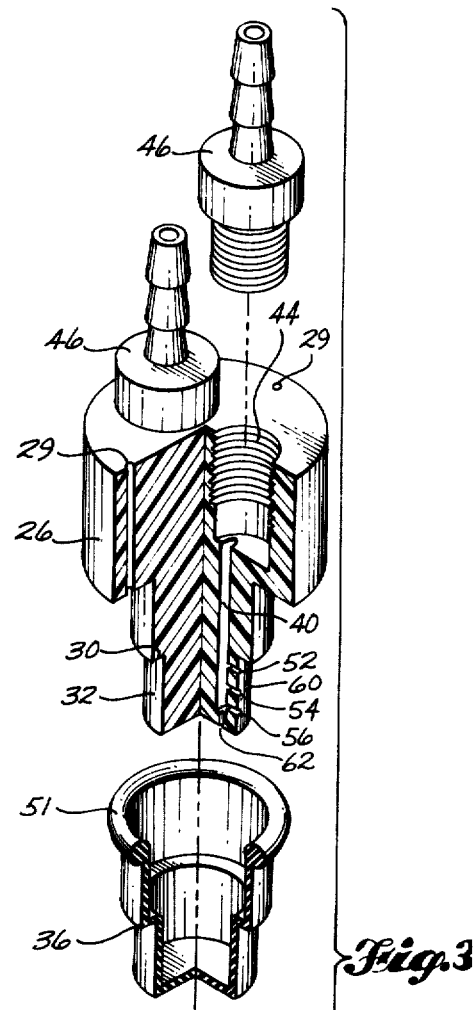
Fig. 3
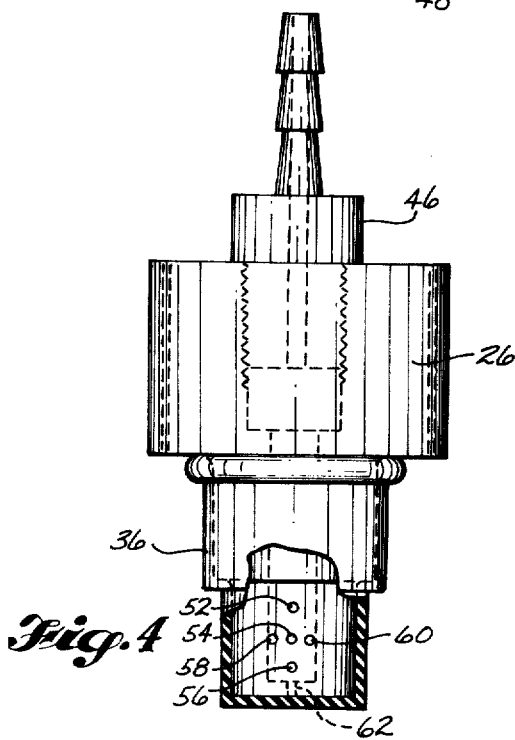
Fig. 4
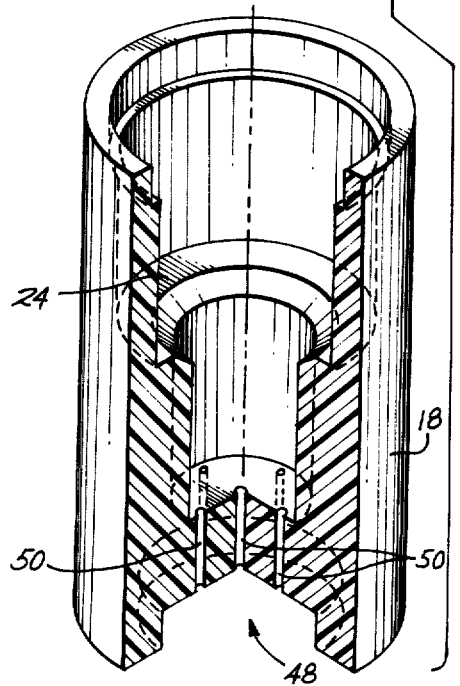

PRESSURE SENSOR

BACKGROUND OF THE INVENTION

1. Field of the Invention

This invention relates to pressure measuring apparatus, and more particularly to a diaphragm type gas operated pressure sensor which is quite small in size, is quick to provide an accurate pressure reading, and is capable of accurately sensing quite large pressures. The sensor has general utility but is particularly well suited for use in a piezometer system for the remote measuring of fluid pressures, such as hydrostatic pressure at various subsurface points in an earthen dam, embankments or in foundations.

2. Description of the Prior Art

Piezometers are known and have been used for many years in situations where it is important to know the stresses at locations which are not conveniently accessible including subsurface hydrostatic pressure. For example, it has long been known that the hydrostatic pressure within an earthen dam is important, and by knowing these pressures a prediction can be made as to whether the dam is performing according to its design specification or whether a fault has developed. Of course, once it is recognized that a fault has occurred at some location within the earthen dam, either immediate corrective measures can be implemented to repair the fault or, in the most extreme situation, advance warning can be provided for evacuation of those people who would be in the path of the torrent of water released by a rupture in the dam.

As is apparent, such pressure measuring systems necessarily involve the implantation of a sensing device in the ground at a distance which is far removed from the surface where the pressure measurements must be read. Direct pressure reading devices, such as gauges or the like, are both expensive and cannot practically be positioned so that they can accurately measure the pressure at the subsurface location, sometimes up to several thousand feet, and still be read at a convenient surface location.

Some prior art piezometers have been of the hydraulically actuated type wherein a remote sensor is positioned at the subsurface elevation, either during construction of a dam or by a drilling operation after construction, and one or more hydraulic fluid lines were provided which extended to the surface. These systems were often unsatisfactory because temperature variations often introduced inaccuracies into the pressure measurement as the result of the hydraulic fluid either freezing or considerably changing in viscosity and specific gravity during such temperature excursions. Additionally, hydraulic fluid, after prolonged exposure to subsurface conditions, tended to decompose creating byproducts which can be corrosive to the remote sensing unit or connecting lines.

Other piezometer systems have used electrically actuated component parts in which pressure fluctuations acting on the remote sensor creates a corresponding variable impedance to an electrical test signal so that an electrical output signal from the remote sensor is proportional to the ground pressure at the sensor location. The sensor is connected by an electrical circuit to a measuring instrument which transposes the electrical output signal into a readable form such as an indication on a meter or chart. These electric piezometers have proven to be somewhat undesirable as the result of their rather high cost, basically due to the expensive remote sensing unit, in addition to a low reliability and projected operating life as the result of the corrosive effect of the soil conditions and/or ground water on the remote sensor unit.

Still other piezometer systems have been of the gas type in which a remote sensor is disposed in the subsurface area of interest and is connected by a dual conduit line to the measuring station on the surface. Of particular interest with respect to this type of piezometer is U.S. Pat. No. 3,388,598, issued June 18, 1968 to Earl B. Hall. The piezometer system described in this patent includes a pressure sensing cell with a bearing wall into which two spaced-apart passageways open. A planar metal diaphragm is normally seated against the bearing wall by the ground pressure being sensed. The internal passages within the load cell are connected by an inlet and outlet conduit which lead to the surface. To measure the hydrostatic pressure at the subsurface location, a supply of gas, under pressure greater than the pressure to be sensed, is connected to the inlet conduit by a valve which varies both the flow rate and pressure of the supplied gas. A pressure gauge is also connected to the inlet conduit and a gas flow meter is connected to the outlet conduit. When gas from the high pressure supply passes through the inlet conduit to the diaphragm at a pressure sufficiently high to unseat the diaphragm by a predetermined distance, this separation will be reflected by a certain flow rate of gas at the flow meter on the surface. At this point the pressure gauge then indicates the pressure against the diaphragm, and hence, the subsurface hydrostatic ground pressure in the area of the remote sensor.

A particular problem of a remote sensing unit of the type disclosed by this patent is that the metal diaphragm must be constructed quite large in diameter to give it sufficient flexibility to enable it to move from a closed to an open position. A large diameter results in the diaphragm displacing a substantial amount of liquid when it does move. The liquid displaced by the diaphragm does not quickly flow back into the soil because of a low permeability condition of the soil. As a result, displacement of the large diameter diaphragm increases the external pressure acting on the diaphragm and this results in an inaccurate reading. In some soils it takes a substantial length of time for the pressure signal generated by the diaphragm displacement to dissipate so that only the hydrostatic ground pressure is being measured.

Prior to making the present invention, I attempted to solve the problems experienced by the prior pressure sensors by making the diaphragm out of an elastomeric material and in the shape of a cup. Initially, I constructed the cylindrical support member for such diaphragm, which was constructed to fit snugly inside of the diaphragm, to include an axial row of three radial inflow ports and a diametrically opposed axial row of three radial outflow ports. Such sensor proved to be unreliable. It resulted in erroneous readings that were sometimes positive and sometimes negative and the diaphragm would oscillate. I attempted to solve these problems by adding a single axial port leading from the inflow passageway towards the end of the diaphragm, but this did not solve the problems. The return rate for these sensors fell within the range of 55 to 80 percent, making a change in design of the sensor a necessity.

SUMMARY OF THE INVENTION

The pressure sensor of the present invention is basically characterized by a support member having an axially elongated cylindrical end portion and a cup-shaped elastomeric diaphragm mounted onto said support member, as in my earlier design, and by an unique port pattern. Such diaphragm includes an outboard portion which is snugly fitted over the cylindrical end portion of the support member. The outer surface of such outboard portion of the diaphragm is in use subjected to a pressure to be measured. A fluid seal is established between an inboard portion of the diaphragm and the support member. The outboard portion of the diaphragm is free of attachment to the cylindrical end portion of the support member so that it can move relative to it. A gas delivery passageway extends through the support member. Gas delivery port means extend outwardly from the gas delivery passageway through the end portion of the support member towards a wall part of the outboard portion of the diaphragm. The support member also includes a gas return passageway therein and gas return port means which extend from another wall part of the outboard portion of the diaphragm into the gas return passageway. The outboard portion of the diaphragm normally overlies and substantially closes both the delivery port means and the return port means but is free to bulge outwardly during use in response to gas pressure within the passageways, an amount sufficient to open both of said port means and allow flow between the gas delivery port means and the gas return port means.

According to an aspect of the invention, the port means includes both side wall radial ports and end wall axial ports, dividing the flow path of the fluid from the delivery ports to the return ports into three distinct parts.

Gas, under pressure, is fed into the delivery passageway and through the sensor, causing expansion of the cup-shaped diaphragm until a predetermined flow rate is achieved. In this null or balanced condition, the pressure of the measuring gas on one side of the cup-shaped diaphragm equals the hydrostatic pressure on the opposite side of the diaphragm. Hence this back pressure is easily read on the pressure page at the surface station, the ambient or subsurface hydrostatic pressure acting on the pressure sensor can be determined.

According to another aspect of the invention, a small dimension, precision pressure sensor is provided which has a low volumetric displacement.

According to yet another aspect of the invention a pressure sensor is provided with a novel configuration of internal components which require no initial calibration or other calibration during its operating life, and yet it exhibits a high degree of accuracy which is unaffected by size deviation within normal manufacturing tolerances.

According to another aspect of the invention, a remote pressure sensing apparatus is provided which is formed from a number of easily manufactured, corrosive resistant, low cost component parts capable of operation over a large range of hydrostatic pressures with a high degree of accuracy.

BRIEF DESCRIPTION OF THE DRAWING

FIG. 1 is a schematic of a piezometer system illustrating a pressure sensing apparatus according to the instant invention disposed in a bore hole of an earthen dam and connected to a surface station so that the subsurface hydrostatic pressure can be measured;

FIG. 2 is an enlarged sectional view of the pressure sensor of FIG. 1;

FIG. 3 is a pictorial view of the presusre sensor of FIG. 2 illustrating the component parts in an exploded configuration, some parts with cut-away portions;

FIG. 4 is an elevational pictorial view illustrating the cup-shaped diaphragm seated on its support member, including a cut-away portion illustrating the positioning of one set of orifices;

FIG. 5 is a fragmented view of the diaphragm end portion of the pressure sensor illustrating a null or balanced condition at which time the hydrostatic ground pressure is measured;

FIG. 6 is a cross-sectional view, taken substantially along line 6—6 of FIG. 5;

FIG. 7 is a pictorial view, taken from above and looking toward the delivery port region of the sensor, when a gas is flowing through the sensor; and FIG. 8 is a view like FIG. 7, but looking toward the return port region of the sensor.

DETAILED DESCRIPTION OF THE PREFERRED EMBODIMENT

As shown by FIG. 1, a piezometer system for remotely measuring a fluid pressure is shown to include a surface station 10 connected to a below ground pressure sensor 12 by a dual passageway fluid conduit 14. The sensor 12 may be buried within an earth dam or the like. It may be one of a plurality of such sensors 12 and conduit 14 may be provided with a quick connect - disconnect coupling 16 so that a single surface station 10 can be utilized for all of the sensors 12.

Referring now to the other figures of the drawing, the pressure sensor 12 may comprise a housing 18 formed to include a first inner cavity 20 of a reliatvely large first diameter in axial communication with a smaller diameter second cavity 22, resulting in a radial shoulder 24 existing between the cavities 20, 22. As illustrated, the radially inward portion of the shoulder 24 may be chamfered.

An inner body or support member 26 is located within housing 18. It is shown to comprise an enlarged first portion 28 that is sized to be snugly received within the first cavity 20. Body portion 28 is preferably constructed to include an axial passageway 29 extending therethrough downwardly to the region of the shoulder 24. During assembly of the sensor 12 an adhesive is injected through this passageway 29 and is used to firmly bond the support member 26 to the housing 18.

Support member 26 includes a cylindrical part 30 which projects into the smaller diameter cavity 22. Cylindrical part 30 includes a reduced diameter end portion 32 which when the support member 26 is in place within the housing 18 is spaced both radially inwardly from the wall of cavity 22 and axially from an end wall of cavity 22. this construction defines a cup shaped chamber 34 in which a pressure signal to be measured is received during operation of the sensor 12, as will be hereinafter described in some detail.

Support member 26 is formed to include a pair of identical axial passageways 38, 40. Passageway 38 is a delivery passageway and passageway 40 is a return passageway. At their upper ends (as illustrated) the passageways 38, 40 communicate with internally threaded enlarged diameter ports 42, 44, respectively. Ports 42, 44 receive threaded portions of identical fittings 46, each having an opposite end portion which is adapted to fit into and grip an end portion of a flexible conduit. The aforementioned dual passageway conduit 14 comprises a pair of flexible tubular conduits. One of them delivers gas from the surface station 10 and is connected to the fitting 46 for the delivery passageway 38. The other connects to the fitting 46 which leads from the return passageway 40 and serves to return the gas to the surface station 10.

The lower end (as illustrated) of the housing 18 is shown to include an end wall provided with a plurality of axial passageways 50, communicating with an end recess 48.

A cup-shaped elastomeric diaphragm 36, which may be fabricated from a Nitrile - Rubber (Buna N), extends over the cylindrical part 30 of support member 26. It includes an open ended inboard portion terminated at a circumferential lip 51 and a closed ended outboard portion. The outboard portion of diaphragm 36 is snugly fitted over the cylindrical end portion of support member 26. The outer surface of diaphragm 36 is subjected to any fluid which enters the cup-shaped chamber 34. The inboard portion of diaphragm 36 snugly fits over the intermediate portion of support member 26. As illustrated, when the parts are assembled, it is clamped between the part 30 and the side wall of cavity 22. Circumferential lip 51 is actually compressed so that it provides a fluid type seal between the inboard portion of the diaphragm 36 and the support member 26.

According to the invention, gas delivery port means extend outwardly from the gas delivery passageway 38 through the end portion of member 30 towards a wall part of the outboard portion of diaphragm 36. Such end portion of support member 26 also includes gas return port means extending inwardly from another wall part of the outboard portion of diaphragm 36 to the gas return passageway 40. The outboard portion of diaphragm 36 normally overlies and substantially closes both the delivery port means and the return port means but is free to bulge outwardly during use in response to internal gas pressure, an amount sufficient to open both of said port means and allow flow between the gas delivery port means and the gas return port means.

According to an aspect of the invention, the gas delivery port means and the gas return port means are identical. The gas delivery port means may comprise a plurality of radial ports 52, 54, 56, 58, 60 and preferably also at least one axial port 62. Similarly, the gas return port means may comprise a plurality of radial ports 52, 54, 56, 58, 60 and at least one axial port 62. As best shown in FIG. 6, when radial ports 58, 60 are included, the outer wall of each passageway 38, 40 is made to be concentric with the outer surface of the cylindrical end portion of the support member 30. This is so that all of the ports 52, 54, 56, 58, 60 will be of the same length. In some installations the ports 58, 60 may be omitted, and the passageway 38, 40 can have a different shape, e.g. they can be circular in cross section. In such an embodiment the radial ports would all be in a common axial plane.

An important specific aspect of the present invention is the division of flow which occurs due to the placement of the ports 52, 54, 56, (58 and 60 when included) and 62. As best shown by FIGS. 7 and 8, the gas flowing outwardly through the gas delivery ports is divided into two substantially equal paths traveling in opposite directions circumferentially about the cylindrical end portion of support member 30. Such flow combines again in the region of the gas return ports. A third flow path is established at the end wall of the diaphragm, from gas delivery port 62 over to gas return port 62. It has been found that when such ports are properly sized and spaced (which is something that can be easily determined in practice) the elastomeric diaphragm does not "flutter". Thus, it is possible to make the diaphragm out of a thin walled elastomeric material. Also, the cup shape of the diaphragm 36 results in it being possible to construct the sensor 12 to have a relatively small diameter. Also, the displacement of the diaphragm 36 by the gas flowing through the sensor 12 is relatively small and does not create a false pressure increase of any substantial duration. This enables the user to move relatively fast from one sensor to another with the surface unit 10. He need not connect the surface unit 10 to a sensor and then stay there for a considerable length of time to wait until the fluid displaced by the diaphragm has slowly seeped back into the ground so that only hydrostatic pressure is being measured.

In a typical installation of the type illustrated, all of the radial openings are equally spaced apart at a distance of about one-sixteenth of an inch. Preferably, all of the ports measure approximately 0.0135 inches in diameter.

Referring again to FIG. 1, the operation of a piezometer system including a pressure sensor 12 of the instant invention will now be described in one environment of intended use, the measuring of subsurface hydrostatic pressure. As is seen, most often pressure sensor 12 is not placed in direct contact with the soil, but rather, it is separated from the earth surrounding a bore hole to prevent foreign material from entering the fluid inlet of the pressure sensing capsule. For a bore hole installation, sand 64 may be initially poured into the bore hole until the bottom is filled with sand approximately six inches in depth. Pressure sensor 12, encased in a canvas bag 66 also filled with sand, is then lowered into the bore hole with flexible conduit 14 attached thereto and additional sand is poured into the opening until the canvas bag has been completely covered with sand. Bentonite pellets 68 are finally dropped into the bore hole on top of the sand pack to make, upon expansion when exposed to water, a water tight seal which closes off the bore hole isolating pressure sensing capsule 12 from the effects of the water column above the seal.

As is seen, surface station 10 includes a supply tank 70 of a suitable high-pressure operating gas, preferably nitrogen, having a shut-off valve 72, regulator valve 74, pressure gauge 76, flow controller 78, bypass valve 79 and flow meter 81. Flow controller 78 is designed to deliver operating fluid from its outlet end at a constant flow rate and this flow rate is relatively unaffected by changes in back pressure. An example of such a flow controller would be that disclosed in my pending patent application Ser. No. 651,360, filed on Jan. 22, 1976, and entitled "Constant Flow Valve For Low Flow Rates".

As mentioned above flexible conduit 14 has dual passageways, each being connected at its outward end to one of the tube couplings 46 on pressure sensor 12 at the bottom of the bore hole. Conduit 14 may be constructed from a heavy polethylene or other such material is substantially corrosion-resistant, yet relatively strong and long lasting in use.

Pressure sensor 12 operates on a null or balanced principle whereby the hydrostatic pressure at the subsurface level is precisely balanced by the pressure of the operating gas from a surface station at a given flow rate.

To determine the hydrostatic pressure in pressure chamber 34, valve 72 is open to provide a flow of operating gas from supply tank 70 to regulator 74 so that the pressure of the operating gas can be reduced to a lower and constant operating pressure level. The precise operating pressure is a non-critical parameter except that it must be greater than the subsurface hydrostatic pressure being measured. From the regulator, the operating gas is directed to flow controller 78 which provides at its outlet end a constant low flow of operating gas that is relatively unaffected by variation in back pressure. The operating gas is then delivered via one passageway in conduit 14 to pressure sensor 12 so that the hydrostatic pressure at the subsurface location can be measured.

As the flow of operating gas continues at a constant flow rate, the pressure increases in passageway 38 until it equals the hydrostatic pressure in pressure chamber 34. As is best seen in FIG. 6, at this point there is a null or balanced condition across the cup-shaped diaphragm 36 wherein the back pressure on the upstream side of pressure sensing capsule 12 equals the hydrostatic pressure in pressure chamber 34. The side and end walls of diaphragm 36 are expanded away from stem 32 creating a flow passageway between the sets of orifices on opposite sides of the diaphragm. The back pressure reading on pressure gauge 76 at surface station 10 then stabilizes at a reading corresponding to the subsurface hydrostatic pressure at the location of pressure sensing capsule 12. The continuing flow rate of operating gas injected into the upstream end of the flow path through capsule 12 is equivalent to the flow rate between the two sets of orifices. The operating gas is vented via the return passageway to the surface and through flow meter 81. Pressure gauge 76 dynamically follows subsurface hydrostatic variations in that any fluctuation in the subsurface hydrostatic pressure is recorded on pressure gauge 76 so long as this balanced condition within pressure sensing capsule 12 is maintained. Accordingly, dynamic variations in the subsurface hydrostatic pressure can be observed by taking a consecutive series of readings on pressure gauge 76 or by employing a recording type pressure gauge.

If conduit line 14 is extremely long, the time required to complete a pressure reading can be considerably shortened by utilizing bypass valve 79. With this method, bypass valve 79 is initially opened so that a flow passageway is provided around flow controller 78 for a flow rate of operating gas higher than that normally provided by the flow controller. As the operating gas pressure exceeds the hydrostatic pressure in pressure chamber 34, diaphragm 36 expands to create a flow passageway between the opposite sets of orifices. As a flow of operating gas begins from the downstream end of pressure sensor 12, it is returned to the surface station via the return conduit in line 14. Next, bypass valve 79 is closed and the operating gas passes through flow controller 78 in the manner heretofore described. The reading on pressure gauge 76 begins to drop until the null or balanced condition described earlier is reached. Finally, a reading on pressure gauge 76 is taken which corresponds to the subsurface hydrostatic pressure in pressure chamber 34.

As previously indicated, a significant aspect of the instant piezometer system involves the use of a novel pressure sensing sensor which is extremely stable and reliable over a much wider range of sensed pressures than heretofore possible with prior art piezometer systems. These enhanced characteristics of the instant pressure capsule are due, in part, to the size, location and geometric configuration of the sets of orifices on opposite sides of member 30 in combination with the novel cup-shaped elastomeric diaphragm for accurately measuring the subsurface hydrostatic pressure.

It was found that if there are too many openings of the size indicated in the side wall of stem 30, or if the diameter of each opening is increased substantially, in the balanced condition a larger volume of gas will flow from the inlet passageway through one set of orifices, around the outside wall of the stem, and through the other set of orifices to the return passageway. The increased flow of operating gas was observed to cause oscillations (i.e. "fluttering") of diaphragm 36 and a corresponding fluctuation of the pressure gauge 76 at the surface station.

The axially extending opening in each set of orifices was found to be important to the operation of pressure sensor 12. The single axially extending opening of each set of orifices controls the smooth expansion of the end wall of the cup-like body of diaphragm 36 and provides an overall rapid read capability which is free from transcient fluctuations which introduce error into the piezometer readings. Without an opening at the end of each passageway, excessive pressure is required to initiate the flow and a delay occurs in which the flow rate must stabilize before a reading can be taken.

Although not a part of the instant invention, it should be understood that, as herebefore maintained, the body of pressure sensor 12 is adapted to have a filter disposed in recess 48, over the inlet opening to pressure chamber 34, and it is expected that the pressure sensing capsule would normally be supplied with this filter already installed so that it can be immediately installed in the ground. Such a filter is preferably made from a ceramic or other non-metallic material which is generally not subject to corrosion or deterioration during extended exposure to subsurface soil conditions. The filter is cemented in recess 48 at the outward end of the pressure sensing capsule, and it serves to exclude particles larger than a certain predetermined size, preferably in the order to 50 microns in pore diameter. While all soil particles are effectively excluded, water at the hydrostatic pressure within the surrounding subsurface soil passes through the filter into pressure chamber 34. The extremely small volumetric change in the pressure chamber during the null or balanced condition minimizes reversed liquid flow from the pressure chamber thereby reducing sedimentation on the outer surface of the filter. As would be expected, because there is practically no flow through the filter during repetitive operatins of the piezometer system, there is practically no tendency for the filter to clog in use.

In addition to the piezometer system illustrated in FIG. 1, it should be understood that the pressure sensor of the instant invention is well suited for numerous other types of pressure measuring requirements. For example, the pressure sensor may be driven or hammered into the ground by any available method since its component parts are rugged and not subject to damage by shock or vibration. With a filter installed at the end of the piezometer to protect the pressure chamber from an influx of foreign material, the pressure sensor can be installed in direct contact with the ground. The extremely small volumetric fluctuation within the pressure chamber during the pressure sensing operation means there is neglible reverse flow from the chamber inlet openings.

Of course, it should also be understood that the present piezometer system could also be used to measure any type of fluid, either liquid or gas, and it would function in the manner heretofore described. For example, it can be used for measuring pressure at any point in a tank containing a liquid used in a manufacturing process.

From the foregoing, various modifications, revisions and adaptations of the pressure sensing capsule of the invention will be apparent to those skilled in the art to which the invention is addressed, within the scope of the following claims.

What is claimed is:

1. A pressure sensor, comprising:

a support member having an axially elongated cylindrical end portion;

a cup-shaped elastomeric diaphragm mounted onto said support member and including an inboard portion and an outboard portion which is snugly fitted over the cylindrical end portion of said support member, said outboard portion having an outer surface which during use is subjected to a pressure to be measured;

means establishing a fluid seal between the inboard portion of said diaphragm and said support member, with the outboard portion of said diaphragm being free of attachment to the cylindrical end portion of said support member;

said support member including a gas delivery passageway therein and gas delivery port means extending outwardly from said gas delivery passageway through the end portion thereof towards a wall part of the outboard portion of said diaphragm;

said support member also including a gas return passageway therein and gas return port means extending inwardly through the end portion thereof from another wall part of the outboard portion of said diaphragm to said gas return pasageway;

with the outboard portion of said diaphragm normally overlying and substantially closing both the delivery port means and the return port means but being free to bulge outwardly during use in response to gas pressure within said passageway, an amount sufficient to open both of said port means and allow flow between the gas delivery port means and the gas return port means;

wherein said gas delivery port means comprises at least one axial gas delivery port extending outwardly from the gas delivery passageway to an end wall part of the outboard portion of said diaphragm, and further including at least one axially extending gas return port extending from another end wall part of the outboard portion of said diaphgragm inwardly into said gas return passageway;

wherein said gas delivery port means includes a plurality of radial ports extending from the gas delivery passageway to a cylindrical side wall part of the outboard portion of said diaphragm, and wherein the gas return port returns also includes a plurality of radial ports extending from the gas return passageway to a cylindrical side wall part of the outboard portion of said diaphragm; and wherein the gas delivery ports and the gas return ports are substantially identical.

2. A pressure sensor according to claim 1, wherein said gas delivery ports comprise a plurality of radial ports which are at least axially spaced apart, and wherein the gas return ports comprise a substantially identical pattern of ports diametrically opposite the gas delivery ports, whereby during use gas flowing between the support member and the diaphragm from the gas delivery ports to the gas return ports divides and flows circumferentially about the support member in both directions from the delivery ports.

3. A pressure sensor according to claim 2, wherein said axial gas delivery port and said axial gas return port substantially occupying a common plane with the diametrically opposed, axially spaced radial gas delivery ports and radial gas return ports.

4. A pressure sensor according to claim 3, wherein said radial gas delivery ports comprise both an axial row and a circumferential row of said ports, and wherein said radial gas return ports comprise both an axial row and a circumferential row of said ports.

5. A pressure sensor according to claim 1, comprising an outer housing in which said support member and said diaphragm are received, with the inboard portion of said diaphragm being a cylindrical extension of the outboard portion of said diaphragm, and with said inboard portion being clamped between said housing and said support member, and said housing including a chamber outwardly bounding the outward end portion of said diaphragm for receiving a pressure signal to be measured.

6. A pressure sensor according to claim 1, wherein the inboard portion of said diaphragm is larger in diameter than the outboard portion of said diaphragm, and wherein said sensor includes a housing having an internal cavity in which the support member and the diaphragm are received, with the inboard portion of said diaphragm being clamped between a portion of said support member and a wall portion of said cavity, and with a space portion of said cavity extending around and endwise outwardly of the outboard portion of said diaphragm.

7. A pressure sensor according to claim 1, wherein said support member includes means at the inlet of said gas delivery passageway to receive a gas delivery hose and means at the outlet of the gas return passageway for receiving a gas return hose.

8. Pressure sensing apparatus comprising:

a pressure sensor comprising:

a support member having an axially elongated cylindrical end portion;

a cup-shaped elastomeric diaphragm mounted onto said support member and including an inboard portion and an outboard portion which is snugly fitted over the cylindrical end portion of said support member, said outboard portion having an outer surface which during use is subjected to a pressure to be measured;

means establishing a fluid seal between the inboard portion of said diaphragm and said support member, with the outboard portion of said diaphragm being free of attachment to the crylindrical end portion of said support member;

said support member including a gas delivery passageway therein and gas delivery port means extending outwardly from said gas delivery passageway through the end portion thereof towards a wall part of the outboard portion of said diaphragm;

said support member also including a gas return passageway therein and gas return port means extending inwardly through the end portion thereof from another wall part to the outward portion of said diaphragm to said gas return passageway; and with the outboard portion of said diaphragm normally overlying and substantially closing both delivery port means and the return port means, but being free to bulge outwardly during use in response to gas pressure within said passageways, an amount sufficient to open both of said port means and complete a flow path between the gas delivery port means and the gas return port means;

means for delivering a gas into said delivery passageway and through said sensor at substantially a constant flow rate;

means for measuring the pressure of said gas to in that manner determine the magnitude of the pressure acting on the outer surface of said diaphragm;

wherein said gas delivery port means includes a plurality of radial ports extending from the gas delivery passageway to a cylindrical side wall part of the outboard portion of said diaphragm, and wherein the gas return port means also includes a plurality of radial ports extending from the gas return passageway to a cylindrical side wall part of the outboard portion of said diaphragm;

wherein said gas delivery ports comprise a plurality of radial ports which are at least axially spaced apart; and wherein the gas return ports comprise a substantially identical pattern of ports diametrically opposite the gas delivery ports, whereby during use gas flowing between the support member and the diaphragm from the gas delivery ports to the gas return ports divides and flows circumferentially about the support member in both directions from the delivery ports.

9. Pressure sensing apparatus according to claim 8, wherein said axial gas delivery port and said axial gas return port substantially occupying a common plane with the diametrically opposed, axially spaced radical gas delivery ports and radial gas return ports.

10. Apparatus according to claim 8, wherein said pressure sensor includes an outer housing in which said support member and said diaphragm are received, said housing including a chamber outwardly bounding the outward end portion of said diaphragm, for receiving a pressure signal to be measured.

* * * * *